United States Patent [19]

Furlong

[11] Patent Number: 4,956,628

[45] Date of Patent: Sep. 11, 1990

[54] ELECTRONIC MONITORING OF GROUND CONTACT BY AN ATHLETE'S SHOES

[76] Inventor: Dennis Furlong, Box 1990 Dalhousie, New Brunswick, Canada, E0K-1B0

[21] Appl. No.: 228,036

[22] Filed: Aug. 4, 1988

[30] Foreign Application Priority Data

Aug. 7, 1987 [CA] Canada ................................. 544054

[51] Int. Cl.$^5$ .......................... G08B 23/00; A63B 5/00
[52] U.S. Cl. ................................ 340/323 R; 235/105; 272/100; 340/539
[58] Field of Search ................. 340/323 R, 573, 568, 340/571, 539; 235/105; 272/100; 200/86.5; 455/100; 364/410; 128/779, 782; 36/115, 137, 139

[56] References Cited

U.S. PATENT DOCUMENTS

| | | | |
|---|---|---|---|
| 3,702,999 | 11/1972 | Gradisar | 340/573 |
| 3,777,086 | 12/1973 | Riedo | 340/573 X |
| 3,974,491 | 8/1976 | Sipe | 200/86.5 X |
| 4,510,704 | 4/1985 | Johnson | 235/105 X |
| 4,578,769 | 3/1986 | Frederick | 340/323 R X |
| 4,703,445 | 10/1987 | Dassler | 340/323 R X |
| 4,736,312 | 4/1988 | Dassler et al. | 340/323 R X |
| 4,763,287 | 8/1988 | Gerhaeuser et al. | 340/323 R X |

FOREIGN PATENT DOCUMENTS 0860785  9/1981  U.S.S.R. ............................. 272/100

*Primary Examiner*—Joseph A. Orsino
*Assistant Examiner*—Thomas J. Mullen, Jr.
*Attorney, Agent, or Firm*—Foley & Lardner, Schwartz, Jeffery, Schwaab, Mack, Blumenthal & Evans

[57] ABSTRACT

An electronic monitoring apparatus for detecting and indicating contact and non-contact of an athlete's shoes with the ground has pressure sensitive means on each shoe on the bottom surface. The pressure sensitive means are connected to a signal generator in each shoe, producing signals indicative of contact or non-contact. The signal in one shoe is transmitted to the other shoe, where the signals are combined to actuate an indicator when both shoes are out of contact. The signal generators can also be arranged to produce signals indicative of a heel to toe sequence, in which case the pressure sensitive means on each shoe is divided into two zones, one at the heel and one adjacent the toe area.

16 Claims, 4 Drawing Sheets

ELECTRONIC MONITORING OF GROUND CONTACT BY AN ATHLETE'S SHOES

BACKGROUND OF THE INVENTION

1. Field of the Invention

This invention relates to an athletic shoe and, in particular, to the sensing and indicating of contact between a shoe and the ground.

2. Related Art

In some sports, it is desirable to know the positioning of a shoe relative to the ground. In race-walking, for example, the rules require that competitors always have one foot in contact with the ground. If both feet are off the ground at any time, the motion is considered to be running and the competitor is subject to disqualification.

Visual observation is used by competition officials, but this is very unsatisfactory. A walker can make four or more strides in a second and therefore observation is very subjective and liable to dispute. In other sports, it could be useful to know when contact between a foot and the ground initiated or ceased.

SUMMARY OF THE INVENTION

The present invention provides for detecting and indicating the presence or absence of contact between a shoe and the ground, and also for detecting and indicating the presence or absence of contact between at least one shoe and the ground when the wearer is walking over the ground.

BRIEF DESCRIPTION OF THE DRAWINGS

The invention will be readily understood by the following description of certain embodiments, by way of example, in conjunction with the accompanying drawings, in which.

DETAILED DESCRIPTION OF THE DRAWINGS

Figure 1:
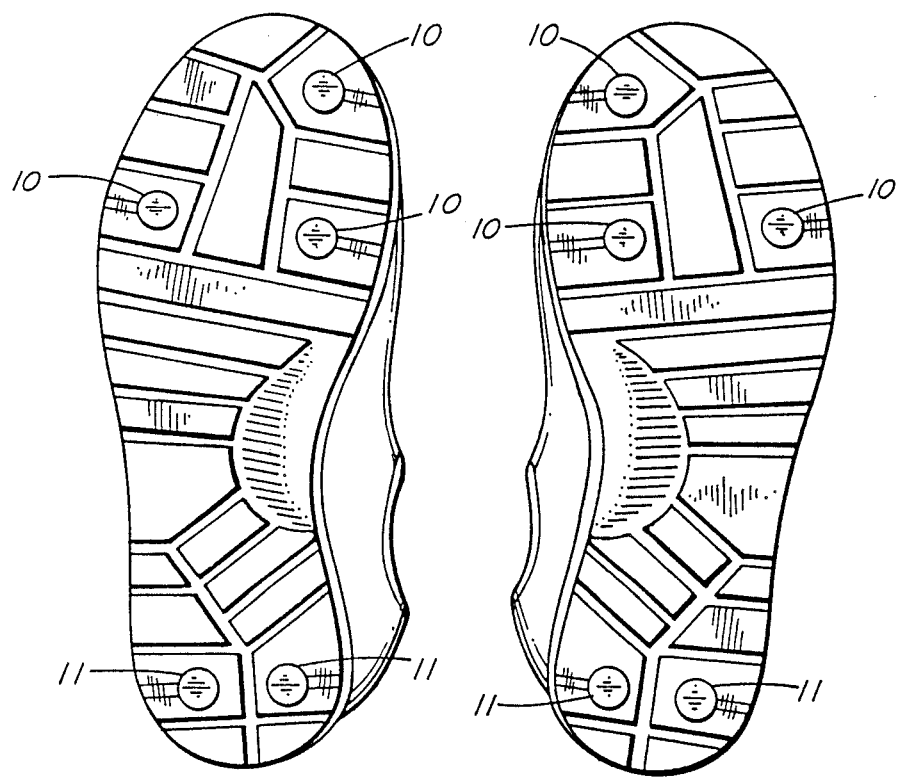
FIG. 1 is a perspective view of the bottom surfaces of a pair of shoes, illustrating one arrangement of sensors.

The operation for determining that one shoe, and foot, is on the ground at all times is as follows. FIG. 1 shows the bottom surfaces of a pair of shoes. Pressure sensors or contact transducers 10 and 11 are shown inserted in the shoes, transducers 10 in the toe region and transducers 11 in the heel region. The transducers are in two groups. In the example, there are three in the toe region and two in the heel region for each shoe. The transducers in each region can be connected in various ways, for example in parallel, or all being connected to separate OR gates.

The arrangement is such that one shoe, for example the left shoe, contains a transmitter which is on when the shoe is completely out of contact with the ground. The other shoe, i.e. the right shoe contains a receiver and circuitry which combines the received signal from the left shoe with a signal developed in the right shoe to trigger an alarm if both shoes are out of contact with the ground.

Figure 2:
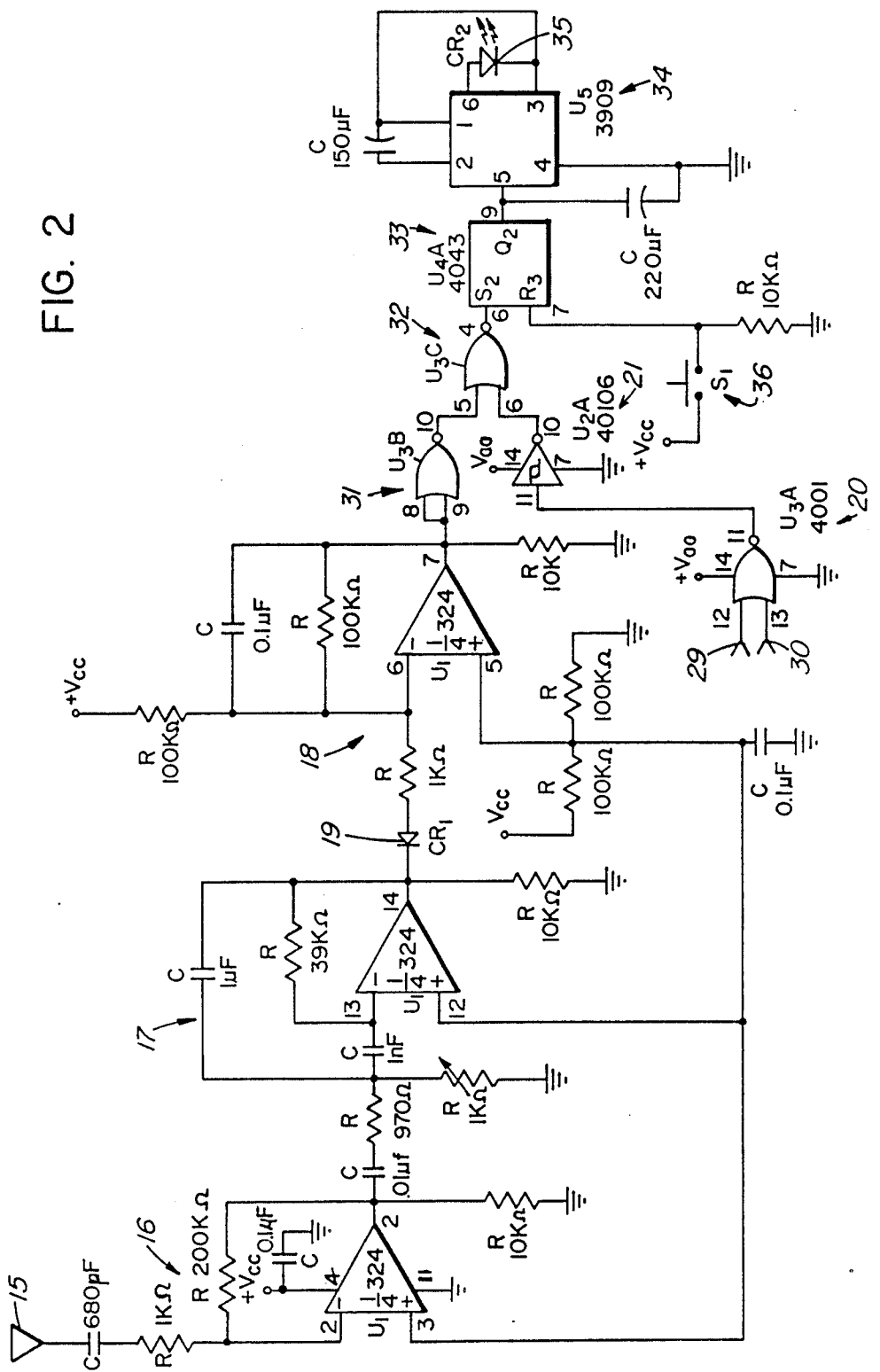
FIG. 2 is a circuit diagram for one shoe for detection of ground status and for detection of a signal from the other shoe.
Figure 3:
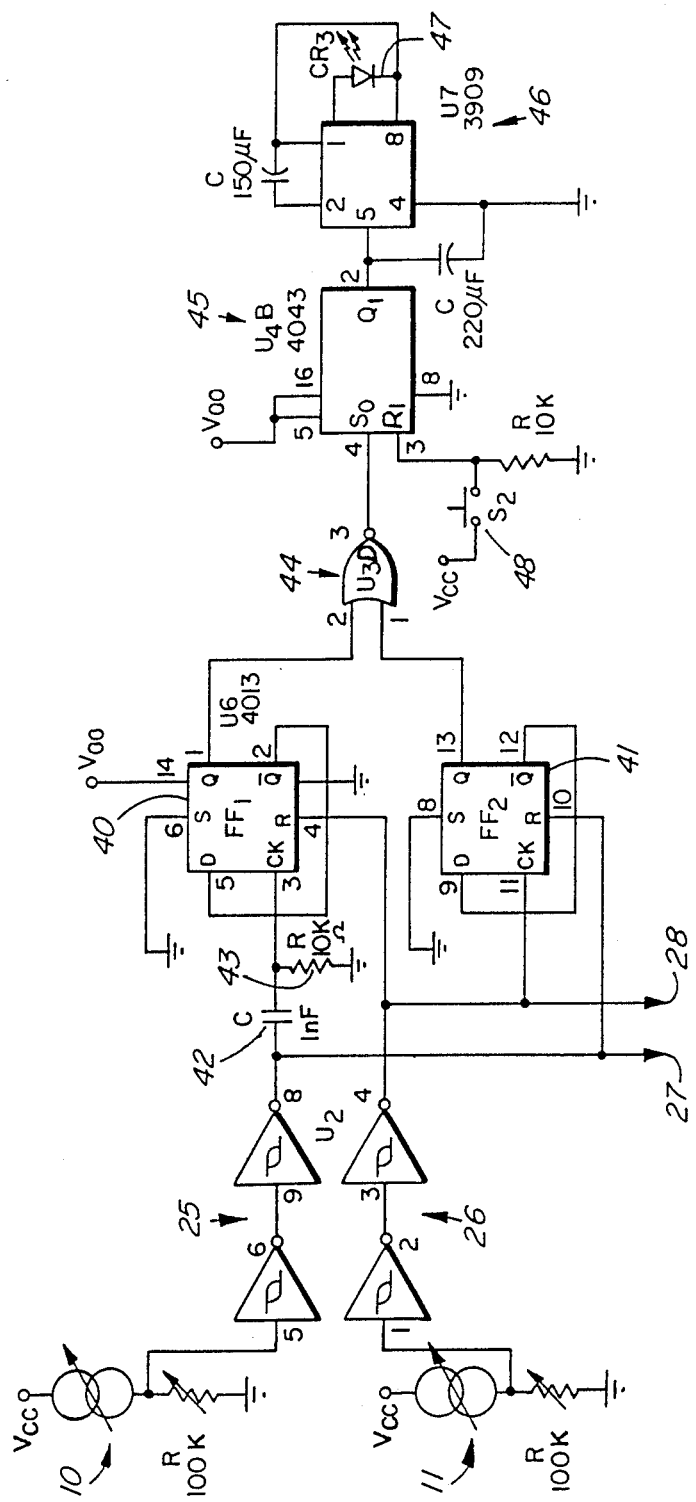
FIG. 3 is a circuit diagram for the same shoe for determining a heel/toe sequence.

FIGS. 2 and 3 illustrate one form of circuitry for, as exemplified above, the right shoe, FIG. 2 being the circuit for detection of a signal from the left shoe and also for the detection of the right shoe on/off ground status. FIG. 3 is the circuit for detecting a heel/toe sequence if desired.

Figure 4:
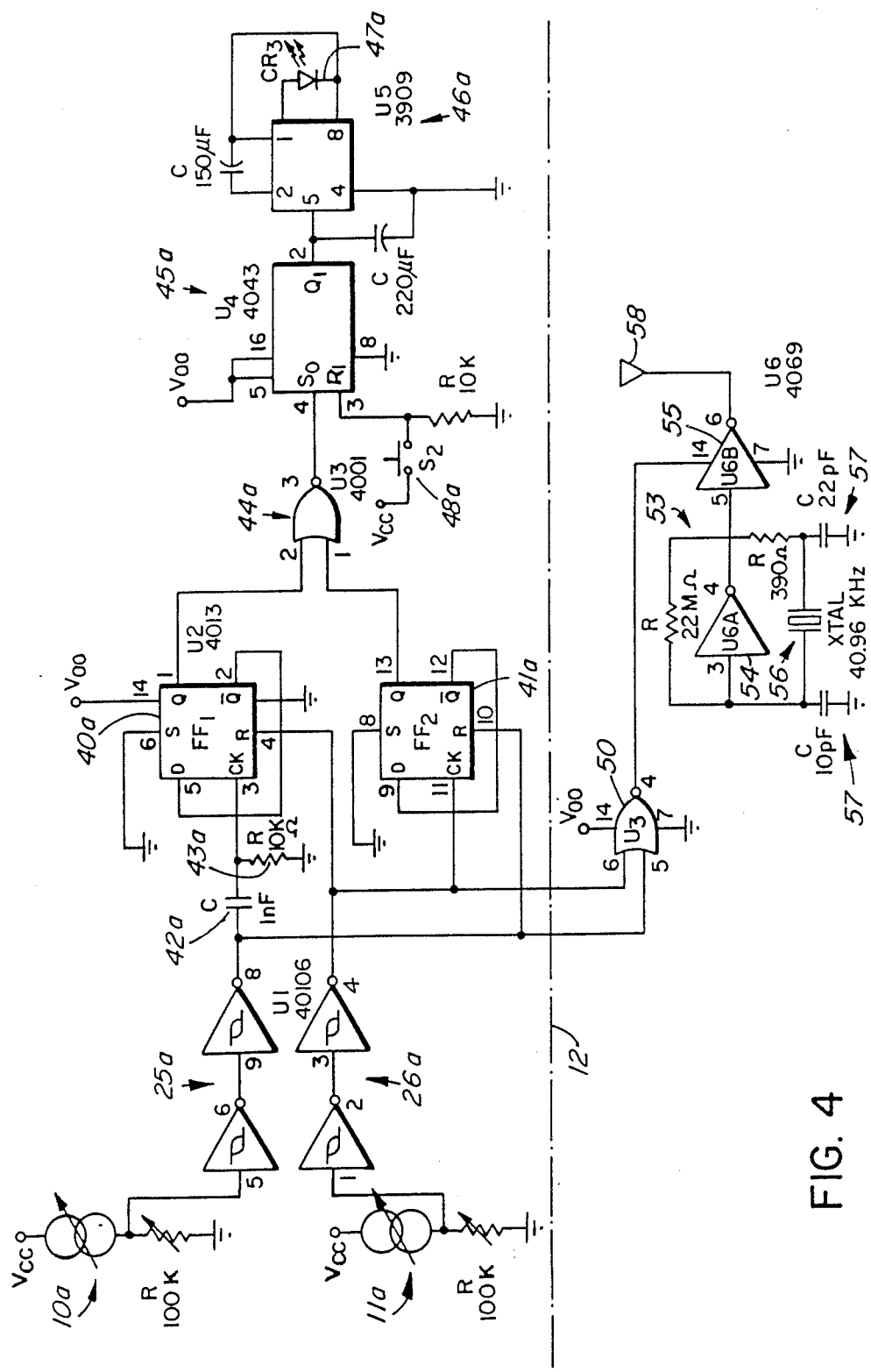
FIG. 4 is a circuit diagram for the other shoe for transmitting a ground status signal to the one shoe.

FIG. 4 illustrates the circuitry for the left shoe. The portion of the circuit above the dashed line 12 is identical to the circuit of FIG. 3 and performs the function of surface contact, and heel/toe sequence for the left foot. The portion of the circuit below the dashed line 12 transmits an RF signal to the other, right, shoe.

In a particular arrangement, discs of pressure-sensitive foam elastomer are used as switch elements. Other arrangements are pressure-sensitive paint or other distributed switching material that creates a signal if under pressure over any portion of its surface.

CMOS (complimentary metal-oxide substrate) integrated circuits are a convenient form. In one arrangement, a 3 volt lithium cell can be mounted on the circuit board for each foot. Normally current draw is in the microamp range, except when an alarm is triggered.

In the following, HI indicates a logical "high" voltage, sufficient to unambiguously change the logic state of the device to which it is applied. LO refers to a voltage low enough to cause unambiguous switching. Typically, for CMOS circuits, these levels are approximately 7/10 and 2/10 of the supply voltage, respectively.

Considering now specifically FIG. 2, the circuitry is for two features: (1) detection of radio frequency (rf) signals from the left shoe — signal is off if the left shoe is completely off the ground; and (2) detection of right shoe on/off the ground status. (The circuitry of FIG. 2 and FIG. 3 is on the right shoe.)

$U_1$ is a quad operational amplifier, one amplifier of which is not used. The first amplifier, nearest antenna 15, and indicated at 16, has a voltage gain of approximately 200. It is followed by a single amplifier bandpass filter, indicated at 17, tuned to the frequency, for example 41 KHz, of the transmitter on the other, left, shoe. The third stage, indicated at 18, is a DC amplifier with a voltage gain of about 100, preceded by a diode 19 to rectify the filtered rf signal. This last stage 18 also filters the DC signal to remove rf fluctuations. Its output is a positive DC signal which is only on if the other, left, shoe is off the ground.

$U_3$ is a quad NOR gate, one gate of which appears in FIG. 3. $U_3A$, indicated at 20, emits a HI signal if both the heel and the toe of the right foot are off the ground (i.e. the right foot is completely off the ground). The output of $U_3A$ is inverted by section A of $U_2$ — a hex Schmitt trigger (a Schmitt trigger is an inverter with hysteresis on the input such that the level required to turn it on exceeds the level at which it subsequently is turned off). Section A is indicated at 21. The other sections of $U_2$ appear in FIG. 3. In the example, the inputs to $U_3A$ come from the circuitry of FIG. 3, being generated by the heel and toe switching circuits which include four Schmitt triggers (the other four sections of $U_2$), to amplify and condition the signals.

In FIG. 3, the switches in the shoe are indicated at 10 (toe region) and 11 (heel region). The switches are connected to the four Schmitt triggers indicated at 25 (toe region) and 26 (heel region), amplifying and conditioning the signals, which are output at 27 and 28, respectively, for connection to inputs 29 and 30, respectively, in FIG. 2. For versions not requiring verification of heel/toe sequencing, the remainder of FIG. 3 can be omitted.

Leaving the above-mentioned remainder of FIG. 3 for later description, the description reverts to FIG. 2, where $U_3A$, item 20, receives inputs at 29 and 30. $U_3B$, item 31, is wired as an inverter and inverts the outputs of $U_3B$ and $U_2A$, item 21. If, and only if, both feet are off the ground, both inputs to $U_3C$, item 32, are LO and $U_3C$ emits a HI, turning on $U_4A$, item 33, which is a latch. If set in this manner, the latch 33 turns on $U_5$, item 34, which is a light emitting diode (LED) driver, wired to flash an LED, indicated at 35. The output of $U_4A$ could also be used to sound a small horn, flash a larger lamp, or in other ways signal that the "at least one foot on the ground" rule had been violated. The latch 33 can be reset by switch 36. This switch must not be accessible to the athlete.

Returning now to the remaining circuitry of FIG. 3, the heel/toe sequence can be verified. Outputs from the Schmitt triggers, 25 and 26, go to two flip-flops (astable multivibrators) $FF_1$ and $FF_2$, indicated at 40 and 41. The signal to the clock (CK) input of flip-flop 40 passes through an RC differentiator, formed by capacitor 42 and resistor 43, which sets the Q outPut of flip-flop 40 HI on the leading edge of the heel signal (when the heel first contacts the ground). The RC differentiator produces a pulse which decays very rapidly (within nanoseconds) after the heel has contacted the ground. Once this pulse has decayed, flip-flop 40 is free to be reset. It is reset by the signal from the toe region, which goes to the R (reset) input of flip-flop 40 and the CK input of flip-flop 41. Flip-flop 41 is set (output at Q HI) whenever the toe switches or transducers 11 are in contact with the ground and cannot be reset—note that a signal from the heel switches or transducers is connected to the R (reset) input of flip-flop 41 until the toe region has left the ground. No differentiator is on the input to flip-flop 41.

Each flip-flop is wired so that if it is in the Q HI state, the next clock input will set it to LO. Thus, if a heel signal follows a heel signal (heel-heel sequence) with no intervening toe signal, the Q outputs of both flip-flops will be LO at the same time. Either of these sequences indicates that the required heel/toe sequence has been violated.

The outputs of the flip-flops 40 and 41 are connected to the inputs of NOR gate $U_3D$, indicated at 44. The output of $U_3D$ goes HI if, and only if, both of its inputs are LO. As explained above, this can only occur if the heel/toe sequence is violated. If the output of $U_3D$ goes HI, the latch and alarm circuit of $U_4B$ and $U_7$, items 45 and 46, is turned on. The latch and alarm circuit is the same as for the "both feet off the ground" detection circuit described above with respect to items 33 and 34 in FIG. 2. An LED is indicated at 47 in FIG. 3. A switch 48 is provided for resetting, as for the circuit in FIG. 2.

FIG. 4 illustrates the circuitry for detecting heel/toe sequence and for transmitting a signal to the right foot. The portion of the circuitry above the dashed line 12 is of the same form as that shown in FIG. 3 and operates in the same manner to detect the heel/toe sequence, and any violation of this. The same reference numerals are used in FIG. 4 as are used for the same items in FIG. 3, with the addition of a suffix (a).

The portion of the circuit below the dashed line 12 transmits an rf signal to the other, left, shoe. Gate 50 has inputs from the circuitry above the dashed line 12, the inputs connected to pins 5 and 6 as indicated at 51 and 52. Gate 50 has a HI output if, and only if, both the heel and toe of the left foot are out of contact with the ground. The HI is applied to the power pin of an inverter $U_6$, indicated generally at 53, comprising two stages or sections $U_6A$ and $U_6B$, indicated at 54 and 55 respectively. The HI applied to the inverter $U_6$ turns on both $U_6A$ and $U_6B$, items 54 and 55. These two inverter stages or sections, together with the crystal 56 and auxilliary components 57, form an oscillator that in the example operates at 40.96 KHz. The square wave output of the oscillator is fed directly to antenna 5B.

In the example described, antenna 58 consists of metal foil in the position of an insole directly under the foot of the athlete. The insole is approximately the size of the athlete's foot and serves to capacitively couple the rf signal to the foot, and the body, of the athlete, who is insulated from the ground by the non-conducting sole of the shoes. The antenna of the receiver, 15 in FIG. 2, in the other, right, shoe is similarly a metal foil insole and through capacitive coupling completes one side of the circuit from transmitter to receiver. Other conductive materials can be used, and the actual shape of the antenna can vary.

The other side of the circuit is formed by radio frequency transmission from the "ground" side of the circuit of the left foot to the "ground" side of the circuit of the right foot. "Ground" in this case refers to the portion of the circuitry shown attached to the ground symbols on the circuit diagrams in FIGS. 2, 3 and 4. These "grounds" are not connected to the earth but are insulated from it by the soles of the shoes and any other insulating material between the circuit boards, one in each shoe, carrying the circuits and the earth.

The rf coupling between the circuit boards can be enhanced by attaching several inches of wire to each board "ground". This wire can be arranged along the side or top of each shoe. It could be formed as part of the shoe during production and could be a metalized strip. The "ground" side of the circuit board and any wire or similar device attached to it must not have a greater capacitance coupling to the body of the athlete than the conductive insole has. This is easily arranged because the circuit board and wire have a small surface area compared to the insole and are not, for the most part, in as close proximity to the foot.

Because the body of the athlete forms one side of the signal path, very little signal is required to transmit from one shoe to the other. Furthermore, transmitters on the shoes of other athletes in close proximity to the receiver on the right foot of the athlete being considered will not interfere with the receiver, even when less than one inch away, because of the lack of a signal path through the body. This prevents signals from interfering with each other and avoids use of coding schemes.

Potential interference from other energy sources is greatly reduced because:

(i) a sharply tuned bandpass filter in the receiver circuit of the right shoe allows only signals within a few percent of the transmitter signal to pass through; and (ii) the signal strength from the desired signal at the input to the receiver is in the millivolt range, and it is unlikely that an interfering signal would be coupled sufficiently to a human body at frequencies below 100 KHz to produce a receiver input signal sufficient to activate any of the circuitry of the shoe.

In the example, the switches in the soles of the shoes, items 10 and 10a, and 11 and 11a, can be for example of foam elastomer. An example of such an elastomer has a resistance in the tens or hundreds of kilo-ohms measured across a quarter inch thickness of a half-inch diameter piece when no pressure is applied. The resistance drops to less than 200 ohms when pressure is applied, as when a person stands on the shoe. This, in conjunction with a 100 kilo-ohm (max.) potentiometer attached to each switching element, generates an unambiguous input to the Schmitt trigger stage, that is, HI if the foot is on the ground and LO if the foot is off the ground. The potentiometers are used to set the transition point for on/off sensing.

In the above description, the terms left foot and right foot are exemplary and it will be appreciated that the arrangement can be reversed, that is, the signal can be transmitted at the right foot and received at the left foot. Also, other means can be provided for the transmission of the signal.

The circuitry can be formed on circuit boards which are attached to the shoes, as by passing the laces of the shoes through suitable holes in the circuit board, or in an enclosure holding the circuit board, and tying the laces over the boards or enclosures. Some form of flexible connection would be required between each board and the insole antenna in each shoe. An alternative is to form the circuitry on boards which can be molded into the heels of the shoes, for example. It is possible that a large degree of encapsulation can be used. The only requirement is that if a visual alarm signal is used, then the signal emitter must be positioned so that it can be seen. It is possible that the alarm signal generator could be remote from the circuit board. If radio transmission is used between shoes, then it can be advisable to provide some means whereby the transmission signals to the alarm signal generator can be coded for different athletes to avoid interference.

The switches in the soles and heels of the shoes can be of suitable material inserted into recesses formed at the time the shoe is manufactured. The connections between the switches and the circuit can be by conductors inserted into grooves formed in the shoe sole and heel, or the conductors can be "molded in" at manufacture. Connections to the antenna can also be "molded in" during manufacture.

The embodiments of the invention in which an exclusive property or priviledge is claimed are defined as follows:

1. Electronic athlete's shoe monitoring apparatus, comprising:
    pressure sensitive means in each shoe of a pair, the pressure sensitive means being reactive to pressure on contact of a shoe with the ground;
    signal generating means on each shoe and connected with said pressure sensitive means for producing a signal indicative of contact conditions between each shoe and the ground;
    transmitting means on one shoe for transmitting the signal generated on said one shoe;
    receiving means on the other shoe for receiving the signal from said one shoe;
    a signal path between said transmitting means and said receiving means, said signal path including a connection through a body of a user; and
    indicating means on said other shoe, said indicating means actuated from both shoes indicative of non-contact between the shoes and the ground, said indicating means including latch means for latching said indicating means ON in response to said non-contact between the shoes and the ground.

2. Apparatus as claimed in claim 1, including means on said other shoe for combining said signals from each shoe and actuating said indicating means.

3. Apparatus as claimed in claim 1, said pressure sensitive means comprising pressure sensitive inserts in the sole of each shoe, pressure on said inserts varying the electrical characteristic of the inserts.

4. Apparatus as claimed in claim 3, said inserts arranged in two groups in each shoe, one group at the heel area and the other group at the toe area.

5. Apparatus as claimed in claim 1, said transmitting means including an antenna in said one shoe, and said receiving means including an antenna on said other shoe.

6. Apparatus as claimed in claim 5, each antenna comprising a conductive layer in each shoe for capacitive coupling to the foot of the wearer.

7. Apparatus as claimed in claim 1, said indicating means comprising a visual alarm device.

8. Electronic athlete's shoe monitoring apparatus, comprising:
    pressure sensitive means in each shoe of a pair, the pressure sensitive means being reactive to pressure on contact of a shoe with the ground;
    signal generating means on each shoe and connected with said pressure sensitive means for producing a signal indicative of contact conditions between each shoe and the ground;
    transmitting means on one shoe for transmitting the signal generated on said one shoe;
    receiving means on the other shoe for receiving the signal from said one shoe; and
    indicating means actuated on the production of signals from both shoes indicative of non-contact between the shoes and the ground;
    said pressure sensitive means being in two spaced zones in each shoe, one zone in the heel and the other zone adjacent to the toe area, said signal generating means in each shoe also including means for producing a signal indicative of a heel to toe sequence.

9. Apparatus as claimed in claim 8, said signal generating means in each shoe including means for producing a signal indicative of a heel to toe sequence combined with said signal indicative of contact conditions between the shoe and the ground.

10. Apparatus as claimed in claim 8, said indicating means actuated also on the production of said signals indicative of violation of a heel to toe sequence.

11. A method of electronically monitoring the contact of an athlete's shoes with the ground, comprising:
    providing pressure sensitive means on the bottom of each of a pair of shoes;
    generating a signal at each shoe indicative of contact between said bottom of said shoes and said ground;
    transmitting the signal from one shoe to a receiver in the other shoe through a signal path including at least one connection through a body of a user; and
    combining said signals to activate and latch on an indicating device on the occurrence of signals from both shoes indicative of non-contact between the shows and the ground.

12. The method as claimed in claim 11, including positioning said pressure sensitive means in two spaced zones in each shoe, one zone at a heel portion and one zone adjacent to a toe portion.

13. A method of electronically monitoring the contact of an athlete's shoes with the ground, comprising:

providing pressure sensitive means on the bottom of each of a pair of shoes;

generating a signal at each shoe indicative of contact between said bottom of said shoes and the ground;

transmitting the signal from one shoe to a receiver in the other shoe;

combining said signals to activate an indicating device on the occurrence of signals from both shoes indicative of non-contact between the shoes and the ground;

positioning said pressure sensitive means in two spaced zones in each shoe, one zone at a heel portion and one zone adjacent to a toe portion; and generating a further signal in each shoe indicative of a heel to toe sequence and combining said signal indicative of contact and said further signal to activate said indicating device on the occurrence of a signal indicative of violation of a heel/toe sequence.

14. The method as claimed in claim 13, including forming said pressure sensitive means in the form of inserts in the bottom of each shoe, the electrical characteristics of said inserts changing with the application of pressure.

15. The method as claimed in claim 14, including providing an antenna in the interior of each shoe positioned for rf coupling with the foot of the wearer.

16. The method as claimed in claim 15, including providing a conductive layer in each shoe, the conductive layers forming said antennae.

* * * * *